(12) United States Patent
Miller et al.

(10) Patent No.: US 6,290,649 B1
(45) Date of Patent: Sep. 18, 2001

(54) ULTRASOUND POSITION SENSING PROBE

(75) Inventors: Steven Charles Miller; Paul Lawrence Mullen, both of Waukesha, WI (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 09/468,989

(22) Filed: Dec. 21, 1999

(51) Int. Cl.[7] .................................................. A61B 08/00
(52) U.S. Cl. ........................................... 600/443; 600/447
(58) Field of Search ..................................... 600/443, 447, 600/444, 425, 649; 356/375; 395/119

(56) References Cited

U.S. PATENT DOCUMENTS

| 5,608,849 | * | 3/1997 | King, Jr. | 395/119 |
| 5,851,183 | * | 12/1998 | Cucholz | 600/425 |
| 5,876,342 | * | 3/1999 | Chen et al. | 600/443 |
| 5,920,395 | * | 7/1999 | Schulz | 356/375 |

* cited by examiner

Primary Examiner—Marvin M. Lateef
(74) Attorney, Agent, or Firm—McAndrews, Held & Malloy, Ltd.; Christian G. Cabou

(57) ABSTRACT

A three dimensional position sensor (24) provides roll, pitch and displacement information to a computer concerning the position of a hand-held object, such as a transducer probe (26). A switch (38) built into the probe is manipulated to alter the image of a subject on a display (18) and also to alter various symbols presented on the display.

24 Claims, 4 Drawing Sheets

| PARAMETER | LOGIQ | CURRENT DEFAULT |
|---|---|---|
| Date | | |
|   Display | On | On —— 54 |
|   Format | M/D/Y | M/D/Y —— 55 |
| Time | | |
|   Display | On | On —— 56 |
|   Format | 24 hr | 24 hr —— 57 |

ULTRASOUND POSITION SENSING PROBE

BACKGROUND OF THE INVENTION

This invention generally relates to the operator interface of an ultrasound imaging system. In particular, the invention relates to means for input of commands for controlling the system modes of operation and for setting selectable system parameters by means of a three dimensional position sensor.

Conventional ultrasound imaging systems are capable of operating in any of a plurality of modes. The most common modes of diagnostic ultrasound imaging include B- and M-modes (used to image internal, physical structure), and the Doppler and color flow modes (the latter two being primarily used to image flow characteristics, such as in blood vessels). In conventional B-mode imaging, ultrasound scanners create images in which the brightness of a pixel is based on the intensity of the echo return. The color flow mode is typically used to detect the velocity of fluid flow toward/away from the probe, and it essentially utilizes the same technique as is used in the Doppler mode. Whereas the Doppler mode displays velocity versus time for a single selected sample volume, color flow mode displays hundreds of adjacent sample volumes simultaneously, all superimposed on a B-mode image and color-coded to represent each sample volume's velocity.

Conventional ultrasound imaging systems provide a two-dimensional image representing the biological tissue in a plane scanned by a probe. A three-dimensional volume can be imaged by moving the probe so that scanning occurs in a succession of scan planes, each scan producing a respective image frame of acquired data.

The probe is typically configured to be held in the hand of the sonographer. A typical probe comprises a transducer array seated in the distal end of a probe housing and an electrical cable penetrating the proximal end of the probe housing. The cable comprises a multiplicity of coaxial wires which connect the elements of the transducer array to the receive channels of the beamformer via a probe/system connector. A conventional transducer array comprises a multiplicity of transducer elements made of piezo-electric material. Typically, each transducer element has metallic coatings on opposing front and back faces to serve as ground and signal electrodes respectively. The signal electrodes are typically connected to respective electrical conductors formed on one or more flexible printed circuit boards (PCBs). The flexible PCBs are in turn electrically coupled to the coaxial wires of the probe cable.

By selecting the time delay (or phase) and amplitude of the voltages applied to the transducer elements, ultrasonic waves can be transmitted which combine to form a net ultrasonic wave that travels along a preferred vector direction and is focused at a selected point along the beam. The same principles apply when the transducer probe is employed to receive the reflected sound in a receive mode. The voltages produced at the receiving transducer elements are summed so that the net signal is indicative of the ultrasound reflected from a single focal point in the object. As with the transmission mode, this focused reception of the ultrasonic energy is achieved by imparting separate time delay (and/or phase shifts) and gains to the signal from each receiving transducer element. A single scan line (or small localized group of scan lines) is acquired by transmitting focused ultrasound energy at a point in the region of interest and then receiving the reflected energy over time.

In the B-mode, for example, the ultrasound image is composed of multiple image scan lines. The brightness of a pixel is based on the intensity of the echo return from the biological tissues being scanned. The outputs of the receive beamformer channels are coherently summed to form a respective pixel intensity value for each sample volume in the object region or volume of interest. These pixel intensity values are log-compressed and scan-converted to form an image frame of pixel data which can be displayed on a monitor. Multiple scans are performed in succession and multiple image frames are displayed at the acoustic frame rate on the display monitor.

In the case where the sonographer is manipulating the transducer probe by hand, one hand is used to control the position of the probe relative to the patient while the other hand is used as necessary to operate levers and keys on the control panel. For example, if the sonographer wishes to select a cut plane in an acquired three dimensional volume, the sonographer depresses a "select" button on the control panel with his free hand. There is a need for an operator interface which is reduces the operator movements required to perform ultrasound examination.

In conventional ultrasound imaging systems, manipulation of three-dimensional images is awkward and non-intuitive, particularly when trying to select cut-planes in an acquired three dimensional volume. Conventional ultrasound systems typically use some combination of one or more knobs and a track ball or mouse. At a minimum, one knob and one track ball or mouse is required to control the cut-plane's three degrees of freedom: roll, pitch, and displacement. The track ball or mouse controls the roll and pitch, while the knob controls displacement. The manipulation required is neither easy nor intuitive. As a result, there is a need for an improved method of manipulating images and other symbols displayed by ultrasound imaging systems.

BRIEF SUMMARY OF THE INVENTION

The preferred embodiment is useful in controlling an ultrasound imaging system using a hand-held object. In such an environment, the preferred embodiment transmits ultrasound waves toward a subject and receives reflected ultrasound waves from the subject, preferably with a transducer array. Image data is generated in response to the reflected ultrasound waves, preferably with a processor. At least a portion of the image data is stored, preferably in a memory. An image representing a portion of the subject is displayed in response to the image data and one or more symbols also are displayed, preferably on a display unit. Position data indicating the position of the object is generated, preferably with a position sensor. A selection signal is generated in response to manual actuation, preferably with a switch. The image and one or more of the symbols are altered in response to the position data and the selection signal, preferably by use of the processor and the display.

By using the foregoing techniques, a user of an ultrasound imaging system can manipulate images in a very intuitive way by scanning a virtual patient or by moving a hand-held object. In addition, the user also can select from a menu and manipulate drawing, tracing and marking for measurement of an image. In general, by using the foregoing techniques, ultrasound images and other displayed symbols can be manipulated with a degree of ease and convenience previously unknown.

DETAILED DESCRIPTION OF THE INVENTION

Figure 1:
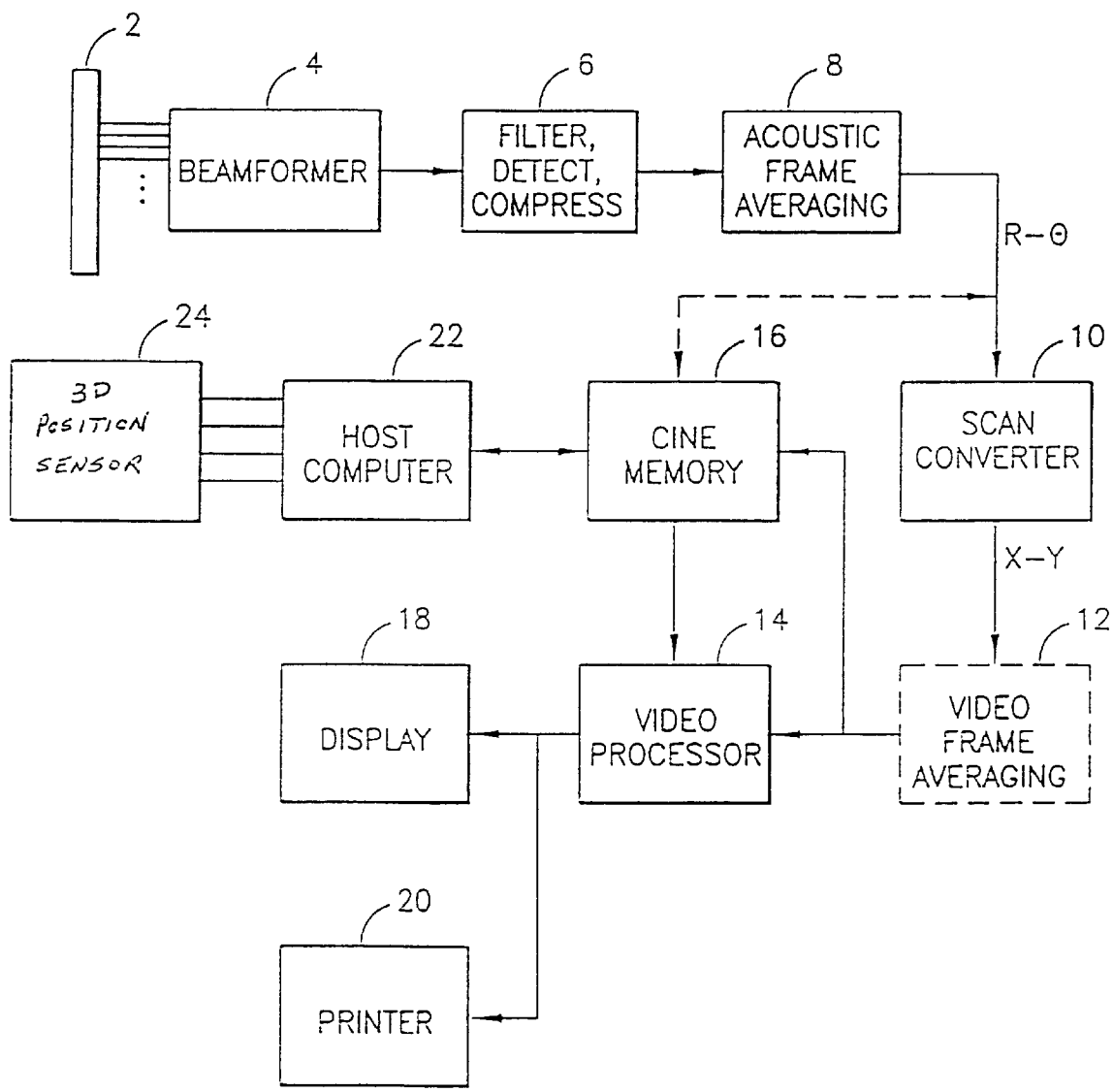
FIG. 1 is a block diagram of a preferred form ultrasound of imaging system incorporating a three dimensional position sensing device and a display.

The basic signal processing chain for a preferred form of ultrasound imaging system is depicted in FIG. 1. An ultrasound transducer array 2 is activated to transmit an acoustic burst of ultrasound waves along a scan line. The return RF signals (i.e., reflected, ultrasound waves) are detected by the transducer elements and then formed into a receive beam by the beamformer 4. The beamformer output data (I/Q or RF) for each scan line is passed through a processing chain 6 which, for the B-mode, includes equalization filtering, envelope detection and logarithmic compression. Depending on the scan geometry, up to a few hundred vectors may be used to form a single acoustic image frame of image data. To smooth the temporal transition from one acoustic frame to the next, some acoustic frame averaging 8 may be performed before scan conversion. The frame averaging may be implemented by an FIR or an IIR filter. In general, the compressed images are in R-θ format (for a sector scan), which is converted by the scan converter 10 into X-Y format for video display. On some systems, frame averaging may be performed on the video X-Y data (indicated by dashed block 12) rather than the acoustic frames before scan conversion, and sometimes duplicate video frames may be inserted between acoustic frames in order to achieve a given video display frame rate. The video frames of image data are passed on to a video processor 14, which basically maps the video data to a gray map for video display on a display monitor 18. A gray-mapped image frame from video processor 14 can also be printed out on a printer 20.

System control is centered in a host computer 22 which accepts position data from a three dimensional position sensing device 24 and in turn controls and synchronizes the various subsystems. (In FIG. 1, only the image data transfer paths are depicted.) During B-mode imaging, a long sequence of the most recent image data are stored and continuously updated automatically in a cine memory 16. Some systems are designed to save the R-θ acoustic images (this data path is indicated by the dashed line in FIG. 1), while other systems store the X-Y video images. The image loop stored in cine memory 16 can be reviewed via position sensor 24 and a section of the image loop can be selected for hard disk storage by sensor 24. For an ultrasound scanner with free-hand three-dimensional imaging capability, the selected image sequence stored in cine memory 16 is transferred to host computer 22 for three-dimensional reconstriction. The plane to be reconstructed and viewed can be selected by sensor 24 by moving a hand-held object, such as transducer array 2. The result is written back into another portion of the cine memory, from where it is sent to the display system 18 via video processor 14. In addition, the host computer may be programmed to control various operating parameters as a function of the current frame (or latest sequence of frames) of video X-Y data. This is accomplished by freezing the current image frame of data via sensor 24 panel, analyzing the data and then setting the appropriate system parameters in accordance with an adaptive algorithm. When adaptive parameter optimization is complete, the user unfreezes the display via sensor 24.

Figure 2:
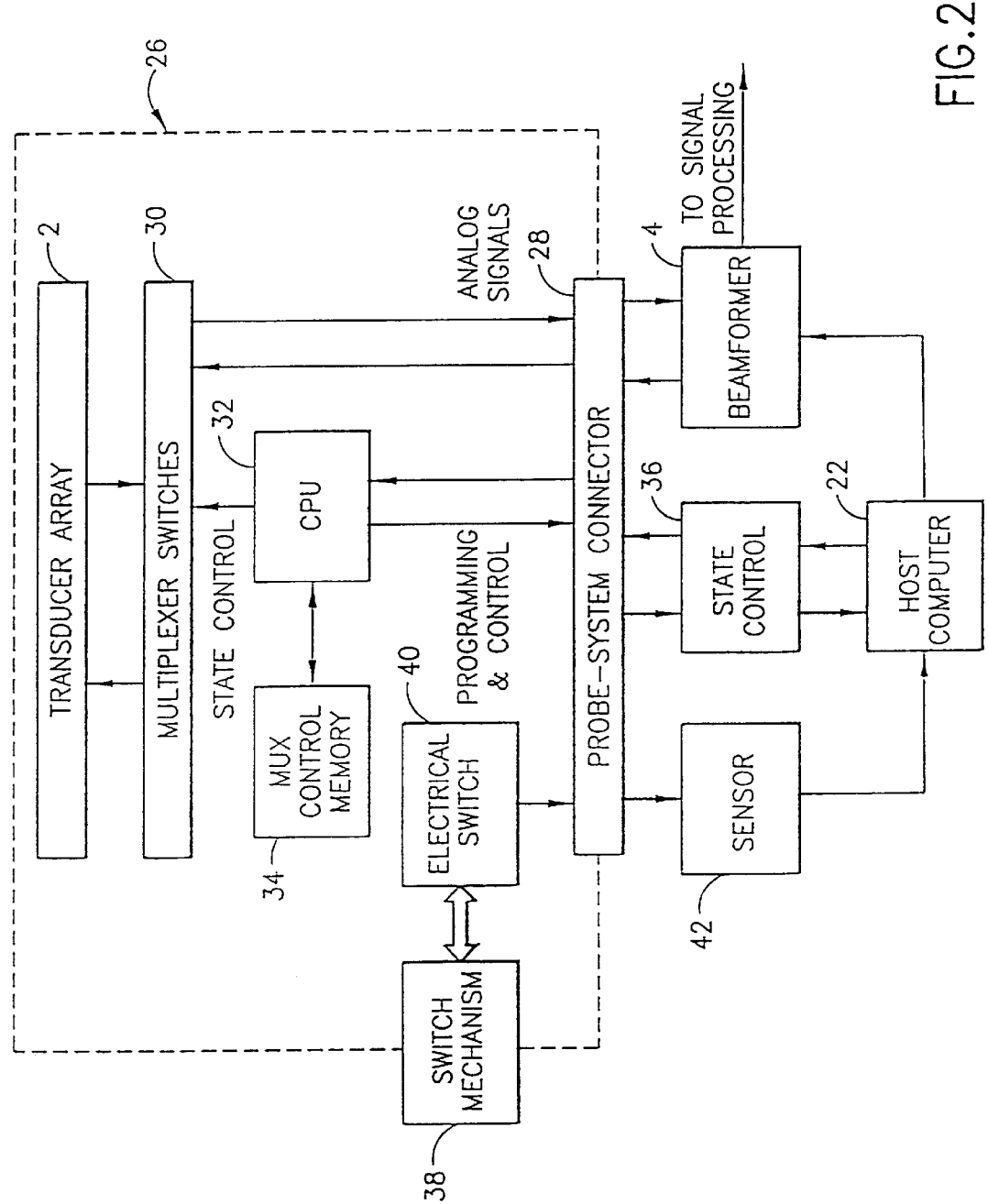
FIG. 2 is a block diagram showing a transducer probe used with the three dimensional sensing device and connected to an ultrasound imaging system in accordance with a preferred embodiment of the invention.

Referring to FIG. 2, a probe 26 (generally indicated by the dashed rectangle) is connected to the imaging system by means of a probe/system connector 28. In the transmit mode, respective analog transmit waveforms are sent from the transmitter of beamformer 4 to respective elements of the transducer array 2 via respective switches of a multiplexer 30 and via respective electrical connections incorporated in the probe/system connector 28. Similarly, in the receive mode, respective analog receive signals representing ultrasound echoes detected by the elements of the transducer array 2 are sent to respective receive channels of beamformer 4 via the multiplexer 30 and the probe/system connector 28. The time delays and other beamforming parameters are changed by the host computer 22 to correspond to the multliplexer state for each image vector acquired. Also, the same multiplexer hardware may be used to scan the active aperture across the array.

The state of multiplexer 30 is controlled by a central processing unit (CPU) 32 incorporated in the probe. The MUX control data is stored in a MUX control memory 34 also incorporated in the probe. A MUX State control signal, which configures the probe with a desired aperture, is output by the host computer 22 to a state control device 36. In response to the MUX State control signal, the state control device 36 sets a register on the probe/system connector 28. The CPU 32 reads that register to determine the desired MUX State and then retrieves the MUX control data corresponding to that state from memory 34. The switches of multiplexer 30 are then set by the CPU.

In accordance with one preferred embodiment of the invention, the transducer probe has an integrated switch which can be operated by the user to implement one or more preselected functions, e.g., a virtual scanning start position. The switch comprises a mechanical element or mechanism 38 and an electrical switch 40, both of which are incorporated in the probe. The electrical switch 40 is electrically connected to a switch state sensor 42 in the imaging system via the probe/system connector 28. In response to appropriate operation of the mechanism 38 by the sonographer, the switch state sensor 42 detects a change in state of the electrical switch 40 and outputs a corresponding selection signal to the host computer 22. The host computer then activates or de-activates the appropriate function in accordance with the current order of prioritized tasks to be performed.

As depicted in FIG. 2, the integrated switch 38/40 is mounted on the probe 26. The switch mechanism 38 may take any one of several different forms. For example, it may take the form of a rocker switch, pushbutton switch, rotary switch, sliding switch, joystick or touch pad. The switch may have two or more positions. In the case of a single-function, two-position switch, the positions may indicate "ON" and "OFF" or similar binary selections. In the case of multiple-function switches, the positions may indicate variable levels of a parameter or the selection of a function or combination of functions. The switch 38/40 may also be implemented as a continuously variable device such as a potentiometer, touch pad or encoder.

Although the switch of the disclosed preferred embodiment is of the mechanical type, in accordance with alternative preferred embodiments the switch activator may be non-mechanical. For example, the state of the electrical switch could be changed in response to receipt of an electrical signal (in contrast to movement of a mechanism) output by a heat or contact-sensitive transducer situated on the exterior of the probe.

Returning to the preferred embodiment shown in FIG. 2, the electrical switch 40 preferably comprises an electrical contact (not shown) which is mechanically linked to mechanism 38. For example, for a single-function switch, the electrical contact may be constructed to bridge a pair of switch terminals inside the electrical switch 40, one switch terminal being connected by one electrical conductor to one terminal of a first electrical connector in probe/system connector 28 and the other switch terminal being connected by another electrical conductor to one terminal of a second electrical connector in probe/system connector 28. The other terminals of the first and second electrical connectors in probe/system connector 28 are respectively connected to a detecting circuit inside the switch state sensor 42. When the electrical switch 40 is closed, a closed circuit across two terminals of the detecting circuit will produce a signal at a third terminal of the detecting circuit, from which the control signal sent to the host computer is derived.

In the case of a multi-function switch, the single electrical switch 40 is supplemented by one or more additional electrical switches, the total number of electrical switches equaling the number of functions. Similarly, the switch state sensor may incorporate multiple detecting circuits to detect the changes in state of the multiple electrical switches, the outputs of the multiple detecting circuits being connected in parallel to the switch state sensor output. In a further alternative, multiple switch mechanisms can be movably mounted on the probe, each mechanism controlling the state of a respective one of the multiple electrical switches.

Figure 3:
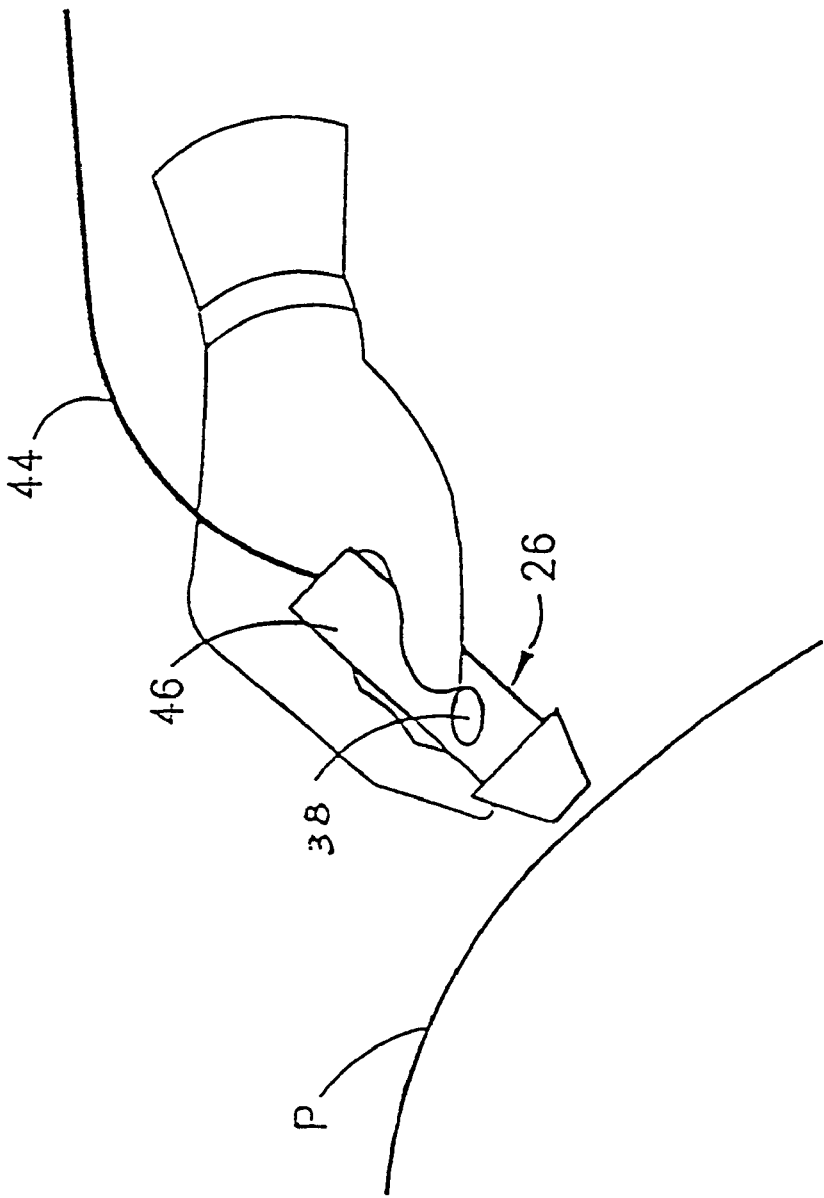
FIG. 3 is a schematic drawing depicting a hand-held transducer probe in accordance with the preferred embodiment.

FIG. 3 generally depicts a transducer being held in the hand of an operator while being pointed at a patient P. The reference numeral 44 indicates the probe cable, while the reference numeral 46 indicates the probe housing. The probe cable 44 comprises a multiplicity of coaxial wires for electrically coupling the transducer array elements to respective switches of the multiplexer, which is preferably mounted on a printed circuit board located near the probe/system connector. One or more of the coaxial wires is dedicated to connecting respective user-operable electrical switches to the probe/system connector. The switch mechanism is mounted so that it either protrudes outside the probe housing 46 or is accessible through an opening in the probe housing. Preferably the switch mechanism 38 is movably mounted on the probe at an ergonomically acceptable location. For example, the switch could be placed at a location which is readily depressed by the thumb or index finger of the operator, as seen in FIG. 3.

In order to use the system described in FIGS. 1–3, a hand-held object, such as transducer probe 26, is moved adjacent a subject being imaged or in free space. The movement of probe 26 is sensed by position sensor 24 in three dimensions, including roll, pitch and displacement. Sensor 24 generates position data indicating roll, pitch and displacement and transmits it to host computer 22 which transmits signals to memory 16 and display 18 in order to alter the displayed images resulting from transducer array 2 and also to alter other symbols displayed on display 18.

Host computer 22 also is responsive to the selection signal resulting from the operation of switch mechanism 38, as well as the position data resulting from sensor 24, in order to manipulate the image and symbols on display 18. image data may represent a three-dimensional volume in a subject being imaged. Host Computer 22 is responsive to the position data, including the roll, pitch and displacement, to identify image data corresponding to cut planes of the three dimensional volume in the subject. Switch 38 is depressed in order to indicate a starting position for the display of the image corresponding to the cut planes. By merely moving probe 26 in three dimensions, the user of the system can indicate the cut planes of the three dimensional space used for displaying a corresponding image on display 18.

Figure 4:
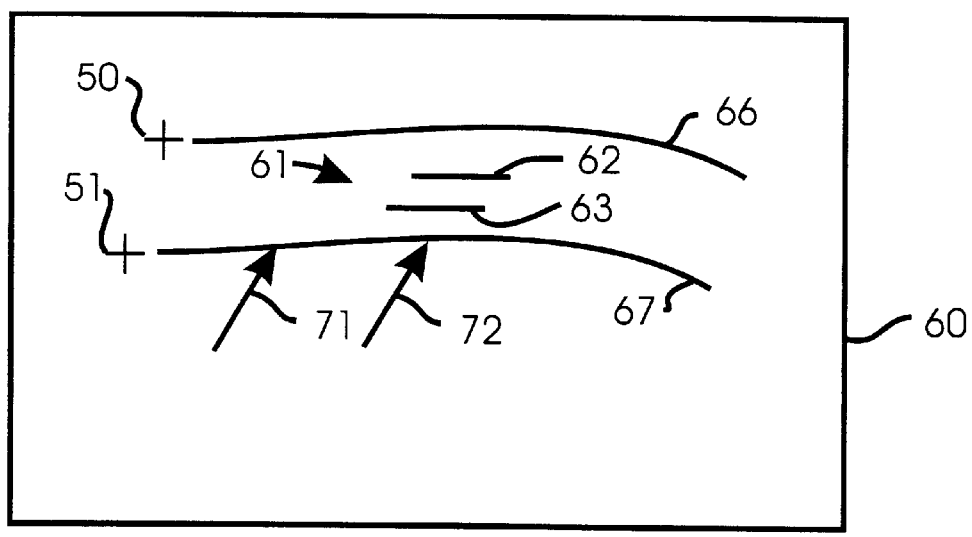
FIG. 4 is a schematic drawing illustrating an exemplary image on the display shown in FIG. 1.

Probe 26 also can be used to perform many functions normally associated with a pointing device, such as a mouse. Referring to FIG. 4, display 18 displays marks used to measure the subject image on display 18, such as cross hair calipers 50–51. By moving probe 26 and manipulating switch 38, the calipers can be manipulated to facilitate the measurement of various portions of the image on display 18. In this case, a user merely moves probe 26 in space as a computer mouse is moved on a table top and manipulates switch 38 in order to alter the calipers displayed on display 18. In a similar manner, probe 26 and switch 38 may be manipulated to annotate the image on display 18.

Display 18 also is used to display functions or menus 52 (FIG. 4) used in order to select various operations of the ultrasound imagine, system. By moving probe 26 in space and manipulating switch 38, various entries from the menu may be selected so that host computer 22 performs the indicated functions. For example, the current default values 54–57 may be modified.

Display 18 also includes the display of a cursor 61 used to indicate various portions of a doppler display 60. The cursor comprises parallel lines 62–63 and can be manipulated by moving probe 26 and depressing switch 38 in order to activate the cursor. In FIG. 4, cursor 61 is used to indicate an area within blood vessel walls 66–67 which are subjected to doppler processing.

Display 18 also typically includes pointers 71 and 72 which are used during demonstrations to identify various parts of the image also displayed on display 18. The pointers can be manipulated and properly oriented by moving probe 26 and can be activated by depressing switch 38.

Three dimensional positions sensors, such as sensor 24, are well known. One exemplary sensor useful in connection with the preferred embodiment is sold under the mark Flock of Birds and is manufactured by Ascension Technology Corp.

The foregoing preferred embodiment has been disclosed for the purpose of illustration. Variations and modifications will be readily apparent to persons skilled in the art. For example, whether the multiplexer is incorporated in the system or in the probe is not important to the practice of the present invention. All such variations and modifications are intended to be encompassed by the claims set forth hereinafter.

What is claimed is:

1. An ultrasound imaging system comprising:
   a transducer array operable to transmit ultrasound waves toward a subject and to receive reflected ultrasound waves from the subject;
   a processor responsive to the reflected ultrasound waves and operable to generate image data;
   a memory storing at least a portion of the image data;
   a display operable to display an image representing a portion of said subject in response to the image data and to display one or more symbols;
   a position sensor operable to generate position data indicating the position of a non-invasive hand-held object; and a selector responsive to manual actuation to generate a selection signal, said processor being responsive to the position data and the selection signal to alter the image and the one or more symbols.

2. The system, as claimed in claim 1, wherein the image data represents a three dimensional volume in the subject, wherein the position data indicates the position of the object in three degrees of freedom, and wherein the processor is responsive to the position data to identify image data corresponding to cut planes of the three dimensional volume in the subject.

3. The system, as claimed in claim 2, wherein the manual actuation indicates a starting position for the display of the image corresponding to cut planes.

4. The system, as claimed in claim 2, wherein the processor identifies image data by indicating addresses in the memory from which image data is to be read for display.

5. The system, as claimed in claim 1, wherein the one or more symbols comprise marks used for measuring the image and wherein the processor is responsive to the selection signal and the position data to manipulate the marks on the display.

6. The system, as claimed in claim 1, wherein the processor is responsive to the position data and selection signal to annotate the image.

7. The system, as claimed in claim 1, wherein the one or more symbols comprise a menu and wherein the processor is responsive to the position data and the selection signal to make a selection from the menu.

8. The system, as claimed in claim 1, wherein the one or more symbols comprise one or more pointers and wherein the processor is responsive to the position data and the selection signal to manipulate the pointers on the display.

9. The system, as claimed in claim 1, wherein the one or more symbols comprise a cursor and wherein the processor is responsive to the position data and the selection signal to manipulate the cursor on the display.

10. The system, as claimed in claim 1, wherein the selector comprises a switch.

11. The system, as claimed in claim 10, wherein the transducer assembly comprises a housing and wherein the switch is located on the housing.

12. The system, as claimed in claim 11, wherein the object comprises the transducer assembly.

13. The system, as claimed in claim 1, wherein the sensor is a three dimensional sensor.

14. A method of controlling an ultrasound imaging system with a non-invasive hand-held object comprising:

transmitting ultrasound waves toward a subject;

receiving reflected ultrasound waves from the subject;

generating image data in response to the reflected ultrasound waves;

storing at least a portion of the image data;

displaying an image representing a portion of said subject in response to the image data and displaying one or more symbols;

generating position data indicating the position of the object;

generating a selection signal in response to manual actuation;

altering the image and the one or more symbols in response to the position data and the selection signal.

15. The method, as claimed in claim 14, wherein the image data represents a three dimensional volume in the subject, wherein the position data indicates the position of object in three degrees of freedom, and wherein the altering comprises identifying image data corresponding to cut planes of the three dimensional volume in the subject in response to the position data.

16. The method, as claimed in claim 15, wherein the manual actuation indicates a starting position for the display of the image corresponding to cut planes.

17. The method, as claimed in claim 15, wherein the altering comprises identifying image data by indicating addresses from which image data is to be read for display.

18. The method, as claimed in claim 14, wherein the one or more symbols comprise marks used for measuring the image and wherein altering comprises manipulating the marks on the display in response to the selection signal and the position data.

19. The method, as claimed in claim 14, wherein the altering comprises annotating the image in response to the position data and selection signal.

20. The method, as claimed in claim 14, wherein the one or more symbols comprise a menu and wherein the altering comprises making a selection from the menu in response to the position data and the selection signal.

21. The method, as claimed in claim 14, wherein the one or more symbols comprise one or more pointers and wherein the altering comprises manipulating the pointers on the display in response to the position data and the selection signal.

22. The method, as claimed in claim 14, wherein the one or more symbols comprise a cursor and wherein the altering comprises manipulating the cursor on the display in response to the position data and the selection signal.

23. The method, as claimed in claim 14, wherein the generating a selection signal comprises switching.

24. The method, as claimed in claim 14, wherein the generating position data comprises generating three dimensional position data.

* * * * *